United States Patent [19]

Klein et al.

[11] Patent Number: 5,326,260
[45] Date of Patent: Jul. 5, 1994

[54] MEDICAL TOOL DISPENSER SYSTEM AND DEVICES

[76] Inventors: Douglas J. Klein, 17681 Crestline Dr.; Paul E. Klein, 928 Lake Shore Rd., both of Lake Oswego, Oreg. 97034

[21] Appl. No.: 7,374

[22] Filed: Jan. 21, 1993

Related U.S. Application Data

[63] Continuation-in-part of Ser. No. 716,308, Jun. 17, 1991, abandoned.

[51] Int. Cl.⁵ .................................................. A61C 3/00
[52] U.S. Cl. ......................................... 433/11; 433/18; 206/63.5; 221/22
[58] Field of Search ............... 433/3, 11, 18; 132/321, 132/323; 206/63.5; 221/22, 70

[56] References Cited

U.S. PATENT DOCUMENTS

| | | | |
|---|---|---|---|
| 3,903,601 | 9/1975 | Anderson et al. | 433/3 |
| 4,004,683 | 1/1977 | Pomeroy et al. | 221/70 |
| 4,034,770 | 7/1977 | Trecker | 132/321 |
| 4,038,753 | 8/1977 | Klein | 433/11 |
| 4,106,374 | 8/1978 | Dragan | 81/302 |
| 4,217,686 | 6/1980 | Dragan | 433/4 |
| 4,277,236 | 7/1981 | Kurz | 433/3 |
| 4,330,271 | 5/1982 | Anderson | 433/3 |
| 4,385,890 | 5/1983 | Klein | 433/4 |
| 4,436,510 | 3/1984 | Klein | 433/4 |
| 4,881,560 | 11/1989 | Blank et al. | 206/63.5 |
| 4,946,385 | 8/1990 | Eckert et al. | 433/18 |
| 4,946,386 | 8/1990 | Kidd et al. | 433/11 |
| 5,013,238 | 5/1991 | Sterrett et al. | 206/63.5 |
| 5,016,766 | 5/1991 | Klein | 221/22 |

*Primary Examiner*—John J. Wilson
*Attorney, Agent, or Firm*—Kolisch, Hartwell, Dickinson, McCormack & Heuser

[57] ABSTRACT

A presenting/dispensing system for orthodontic/medical devices is described, which devices are formed homogeneously in an elongate elastomeric chain, with each device taking the form of an elongate carrier body with a central, elongate finger portion to which is integrally joined a small supply tools, such as O-ring ligators or others. The body is formed in a T-shaped configuration with the finger portion being joined at one of its ends to bar-like handle/positioner/indexing structure.

5 Claims, 1 Drawing Sheet

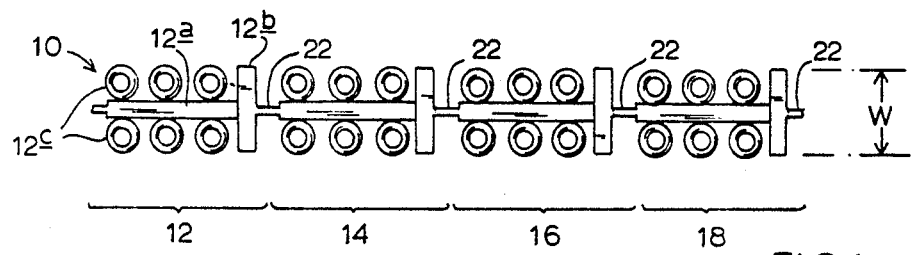
FIG.1
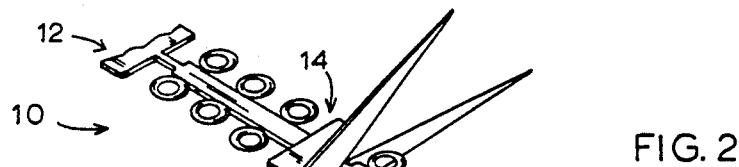
FIG.2
FIG.3
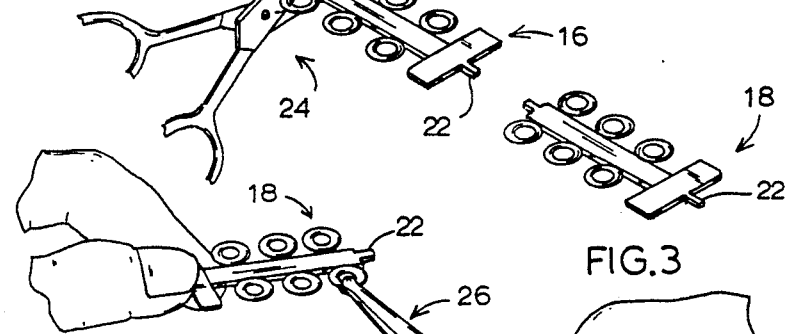
FIG.5
FIG.4

MEDICAL TOOL DISPENSER SYSTEM AND DEVICES

BACKGROUND AND SUMMARY OF THE INVENTION

This is a continuation-in-part of application Ser. No. 07/716,308, filed Jun. 17, 1991, and now abandoned.

The present invention relates to a hand-holdable, tool-dispensing medical device, and to a presenting/dispersing system which may incorporate the same in the form of a spooled or serpentine-folded chain containing plural seriatim-joined devices. More particularly, it relates to such apparatus which is designed specifically for handling to-be-dispensed devices which carry intra-oral orthodontic elastomeric tools, such as ligators, separators and others, a setting in which the invention has been found to offer particular utility. Accordingly, a preferred embodiment of the invention is described in conjunction with dispensing such orthodontic-tool-carrying devices.

Effective elastomeric orthodontic tools of the type generally mentioned above have been available for years, and various techniques, apparatuses and arrangements have been proposed for enabling dispensing of the same. For example, prior-art patents dealing with the latter include U.S. Pat. Nos. 3,903,601 to Anderson et al., 4,038,753 to Klein, 4,330,271 to Anderson, and 5,016,766 to Klein et al.

In the dispensing and handling schemes proposed in the past, there are several common characteristics which, while useful and appropriate in many instances, are not so useful and appropriate in others. For example, ligators, such as O-ring ligators, or separators have been presented in the past (1) as completely free units which are plucked from a container holding the same, (2) as free (non-co-joined) individuals contained on a dispersing wand or the like, (3) in elongate chains of individual, separable units, and (4) in relatively large arrays of units with each one being detachably joined integrally with an elongate element. Examples of the latter are found in the '753 and '271 patents mentioned above.

Generally speaking, practitioners have found useful a handling and dispensing arrangement in which an elongate dispensing body carries integrally joined, but cutaway- or break-away-separable, orthodontic tools.

Interweaving today with the issue of convenient handling and dispensing is the issue of preventing patient cross-contamination resulting from at-risk exposure of intra-oral tools prior to placement for intra-oral use.

Dispensing and handling systems/devices of the type in the past characterized by a long dispensing finger, or rod, containing multiple detachable tools, such as ligators, often include a far greater number of tools than an orthodontist actually requires during a particular patient-specific treatment procedure. Accordingly, there is substantial waste with such conventional systems/devices even when used in a carefully controlled hygienic setting that enables patient-specific dispensing of one or two only of such tools in an exposed environment. That waste results when only a few tools are removed for use, and the remainder are tossed out in keeping with cross-contamination hygiene practice.

Giving an illustration relating to the use of ligators, for example, experiences indicate that there are many procedures (like less-than-full-arch procedures) in which only a very few ligators are required. In the setting of such procedures, it is desirable to be able to place, in an at-risk environment, a dispensing/handling device, which carries only a small number of available ligators, thus to minimize wasteful discarding of exposed but unused ones. Multiple devices each containing small numbers of ligators can always be brought into play where greater numbers of ligators are required for a given procedure, still without leading to excessive waste.

A general object of the present invention is to provide a unique elastomeric, hand-holdable, tool-dispensing device for medical tools, such as orthodontic O-ring ligators or other devices, which takes this latter consideration into account in a very practical, simple, economical and satisfactory manner.

More particularly, an object of the invention is to provide a device, and a system for enabling dispensing thereof, wherein plural tool-dispensing devices (units) are formed preferably unitarily in a elongate chain from which they can be separated easily as individuals. Each device carries but a relatively small number of to-be-dispensed tools, such as ligators, and each device takes the form of an elongate body which carries a small number of integrally formed tools, adjacent one end of which body is formed an integral, digitally manipulable bar-like/handle for control purposes.

According to the system of the invention, such an elongate chain of devices may be stored conveniently either as a spool, or as a folded serpentine "stack", within the interior of a contamination-barrier container for enabling device-by-device withdrawl through a blocking/interference slot, or aperture. In such a setting, the proposed manipulable bar-like/handle functions not only ultimately as control structure in the hands of an orthodontist or other user, but also as a control dispensing/positioning structure under circumstances of such a handle being drawn against the inside of the container adjacent the mentioned blocking/interference slot. In addition, the handle functions as visual-indexing structure—telling the user at a glance how many available tools have been extracted from the dispensing container.

Formed as a homogeneous, unitary object, the elastomeric chain offers an economic solution to manufacturing of devices (prepared in accordance with the invention) for convenient dispensing and use.

These and other objects and advantages which are attained by the invention will become more fully apparent as the description which now follows is read in conjunction with the accompanying drawings.

DETAILED DESCRIPTION OF THE DRAWINGS

FIG. 1 is an enlarged fragmentary plan view of a length of an elongate elastomeric chain containing plural, individually separable orthodontic medical devices constructed in accordance with the present invention.

FIG. 2 is a further enlarged (relative to FIG. 1) isometric view of the chain fragment of FIG. 1, illustrating pre- and post-separation of individual units from the chain via manual scissors-effected separation.

FIG. 3 is a fragmentary isometric view illustrating handling and manipulation of an individual device during a procedure with a patient.

FIG. 4 is a fragmentary isometric view illustrating a presenting/dispensing system including to-be-dispensed devices stored on a spooled chain accessible through a dispensing container via a blocking/interference slot, with a desired device being cut-separable from the chain via a cutter blade positioned on the container outward of the slot.

FIG. 5 is an enlarged, fragmentary, upper-side sectional view taken generally along line 5—5 in FIG. 4, focusing attention to the presenting/dispensing/cutting-/indexing features of the invention.

DETAILED DESCRIPTION OF A PREFERRED EMBODIMENT OF AND BEST MODE OF IMPLEMENTING, THE INVENTION

Turning now to drawings, and referring first of all to FIG. 1, indicated generally at 10 is a fragment of an elongate, homogeneous, unitary, elastomeric chain, which preferably is a molded chain, of plural, tool-dispensing medical devices, each being individually separable, as will be explained, and each carrying plural tools (ligators) for use during an orthodontic ligating procedure. Specifically shown in FIG. 1, in the fragment illustrated, are four such devices, designated 12, 14, 16, 18. Referring for illustration purposes to device 12, each device is characterized by having a carrier body with an elongate, slender, finger-like portion, such as portion 12a, one end of which is joined integrally to elongate, broad-expanse, bar-like, handle/positioner structure 12b. Structure 12b is also preferably flat and planar to promote ease of storing, dispensing and handling. Carrier body 12 has what may be thought of as a T-shaped configuration formed by the joinder of portion 12a with structure 12b. Joined integrally to the opposite sides (top and bottom as shown) of body 12a are six orthodontic O-ring ligators, or tools, such as tools 12c.

The devices in chain 10, other than those devices which, at a given point in time, make up the opposite ends of the chain, are joined seriatim to two other devices through reduced-dimension, or weakened, cut regions, such as those shown at 22 in FIG. 1. The presence of such cut regions is preferable to facilitate device separation, but not absolutely necessary.

The overall width of each device in chain 10, as the same is viewed in FIG. 1, is indicated at W. The reason for mentioning this will become apparent shortly.

As was stated earlier, there are various orthodontic ligating procedures in which it is not necessary that an orthodontist have readably available, and in an exposed environment, enough individual ligators to handle a full arch or more of a patient's mouth. Nevertheless, various prior-art systems which present ligators for dispensing from carrier systems often make available at least a full arch complement (in number) available all at once. Where only a minor number of ligators is actually required for use, and to assure proper guard against patient cross-contamination, carriers bearing a large number of unused ligators are often simply thrown away and thus wasted after such a limited procedure.

Recognized in the underlying implementation of the structure of the present invention is that presentation of dispensable ligators in small groups makes possible proper attention to patient cross-contamination avoidance, as well as to ligator-waste avoidance. While the exact "small" number of made-available ligators is a matter of choice, applicants have found that a very suitable small-number, made-available amount falls within the range of four to six ligators. Accordingly, the preferred embodiment of the invention illustrated herein is constructed to include a number within this range.

Preferably, plural, seriatim-joined devices, containing the small number of ligators just mentioned, are fabricated in the chain fashion indicated in FIG. 1 for manufacturing simplicity and economy, and ultimately for ease of dispensing and handling. Preferably also, a prepared chain of separable devices is designed to be handled in such a fashion that selected devices can be exposed to a contaminating environment only on a device-by-device basis for separation of individual devices for ultimate use.

FIG. 2 illustrates just very generally how separation may occur, in which figure, device 18 has been shown cut-separated from device 16, and device 16 has been shown about to be cut-separated from device 14 by scissors shown at 24. These separation steps will typify a procedure wherein an orthodontist has concluded that he or she will require up to twelve ligators (six per device). Accordingly, two and only two devices are separated from the chain and exposed in the environment where contamination could occur. FIG. 2, which is simply generically illustrative of a separation operation, does not specifically illustrate a contamination barrier to isolate still-to-be-used devices 12, 14, and others (undepicted) in chain 10. A proper contamination barrier for presenting and allowing dispensing will be discussed shortly.

FIG. 3 illustrates how, typically, a separated device, and here device 18 is depicted, is used in the hands of an orthodontist during a ligating procedure. In FIG. 3, the left hand is shown gripping the handle portion of the device, and the right hand is shown employing hemostat 26 to separate one of the six ligators (tools) carried on the carrier body in device 18. Pull-away, or snap-away, separation of each ligator is facilitated by the presence in the units of the invention of relatively small connecting isthmuses (not shown) extending between each ligator and the associated central finger portion of the carrier body. Obviously, the handle portion makes for convenient handling, with the orthodontist not being required directly to touch an about-to-be-removed ligator.

Addressing attention now to a dispensing/presentation container which cooperates with a chain, like chain 10, to afford a system that attends to the matter of patient cross-contamination, and turning attention now to FIG. 4, here there is shown generally at 28 one form of a suitably stand-anchored, plastic dispensing container with partitions dividing the container into dispenser sections, each for holding individual spools of chain like chain 10 of FIG. 1. Three such dispenser sections are shown at 30a–c, and three partitions are shown at 32a–c. A somewhat analogous array of presentation/dispensing containers (for another type of orthodontic apparatus) is illustrated and described in above-mentioned U.S. Pat. No. 5,106,766, and reference is herein made to that patent for the reader's aid in understanding, generally, a similar kind of anti-contamination system. There is no special requirement that spooled chain be used, and those skilled in the art will appreciate that serpentine stacking and other folding techniques are also possible to store chains of medical devices for dispensing in accordance with the present description. Also, an appropriate dispensing/presentation container can be one which has but one, rather than plural, dispenser section(s).

Focusing attention on dispenser section 30a, the same herein includes a suitable, somewhat upright, rectilinear space, within which is stored a chain 34a, like chain 10, with the latter wound on a spool residing within the section. It is a matter of choice whether such a spool is supported or not on a hub. As viewed in FIG. 1, this chain, progressing from the center of the spool, wraps in a clockwise direction from the center toward the outside of the spool, with the end of the chain containing devices next-to-be-dispensed residing near the top of the spool, and extending into what might be thought of as a pre-dispense condition adjacent a blocking/interference slot, or aperture structure, such as $30a_1$ formed in the top of the front of section 30a. Slot $30a_1$ has a width which is less than previously mentioned width W.

Formed adjacent the top of section 30a (and to-be-described sections 30b–c) is resident cutting structure including a sheath-like unit 36 which supports plural cutter blades 38, one blade for each dispenser section. This structure is used, as will be explained, to separate units from respective chains, such as chains 34a–c. Such a cutting structure facilitates single-hand access to, and cut-separation of, selected devices.

Continuing with the description of container 28 in FIGS. 4–5, its top is formed with an access opening 40 defined in part by that portion of the container defining the slots, such as slot $30a_1$, and a generally upright wall-like member 28a. The significance of opening 40 will be described shortly.

Still referring to FIGS. 4–5, the process of withdrawal and removal of a desired number of devices will now be described. The user will encounter a desired spooled chain with a terminal, handle-forward device, such as device $34b_1$ of middle-positioned, spooled chain 34b in section 30b, extending upwardly through opening 40 in a hand- or hemostat-accessible position behind the front of container 28. In the condition now being described, the ligator tools associated with the particular handle which is exposed are just slightly exposed on the outside of the container, and are in conditions not yet handled by the user of the system.

To withdraw and remove, say, just device $34b_1$, the user (orthodontist or assistant) accesses the handle of that device and pulls it forward of the container over slot $30b_1$. While pulling the device forwardly, the user also pulls it downwardly somewhat after the handle clears the slot. By so pulling the finger portion feeds through the slot until further movement is prevented when the handle of the next device in the chain is blocked from exiting the slot due to its width being greater than the width of the slot. This very situation is depicted in FIG. 5 with device $34c_1$ having been drawn through slot $30c_1$ until the handle of next device $34c_2$ is blocked from exiting the slot due to the width of the slot being narrower than that of the handle. To cut-separate device $34c_1$ from chain 34c, the user pulls that device downwardly so that its cut region, such as previously mentioned regions 22 of FIGS. 1–3, is severed by blade 38. The remainder of the chain will stay behind the front of the container and next device $34c_2$ will now be the terminal device in the chain and will extend upwardly like device $34b_1$ shown in FIG. 4.

Of course it should be appreciated that any number of devices may be dispensed as described above. Key features of such dispensing are that one-handed dispensing is achieved, and that only the handle of the terminal device in a chain need be handled by the user. The above-described presenting/dispensing system also offers the advantage of preserving usability of unremoved devices in a chain, because such devices are not allowed to move forward of the container into the at-risk, contamination-causing environment.

It should also be appreciated that situations with dispensing sections, somewhat like sections 30a–c, but not including associated separating-blade structure, the user may simply use scissors or the like for manual separation.

In the dispensing process now described, the handle portions, during pull-up-and-out-dispensing, act as a physical positioning structure—such functionality forcing somewhat of a "pause" between exposure of adjacent devices, thus to inhibit undesired exposure of a not yet-to-be-used device. In addition, the handle portions also act as a visual indexing means—serving as a quick visual reference to the user of exactly how many available ligators have been exposed.

It should now be apparent, from the description which has just been given above, that the system of, and the devices provided in, the present invention offer many advantages. The individual devices are formed conveniently with a carrier body that includes a user-manipulable bar-like handle from which projects a slender finger portion containing a small number of ligators that can be used conveniently in low-number ligation procedures. Conveniently, these units are formed homogeneously in an elongate chain which can be dispensed from a spooled or folded condition stored within the anti-contamination environment of a protective container.

Device-by-device dispensing is especially facilitated by the positioning coordination and cooperation which occurs between the presentation/dispensing apertures formed in the container in association with each dispensing section, and the respective handle portions formed in the devices. Further, handle structure exposed on the outside of the dispensing container offer a quick visual index and reference to a user of just exactly how many ligators (or other tools) have been exposed for separation and use.

Patient cross-contamination is held to a minimum, as is also unnecessary waste of unused but contamination-exposed tools.

While a specific illustration of the invention has been presented herein showing orthodontic ligators as the tools which are carried for use, and while certain other kinds of tools have been mentioned, it should be apparent to those skilled in the art that the apparatus of the invention is useful for the presentation, dispensing and handling of a variety of medical tools.

Accordingly, while a preferred embodiment of the invention has thus been described herein, one skilled in the art will recognize that certain variations and modifications may be made without departing from the spirit of the invention.

It is desired to claim and secure by Letters Patent:

1. A chain of elongate, homogeneous, hand-holdable, tool-dispensing medical devices that can be dispensed from an associated dispenser for cut-separation of a desired device from the chain, comprising:

plural, interconnected, cut-separable, elongate carrier bodies, with each of said bodies including a supply of medical tools formed integrally with and detachably joined to it;

each of said bodies also having digitally manipulable handle-positioner structure formed integrally with it adjacent one end thereof, said handle-positioner structure having dimensions sufficient for cooperating with the dispenser to position an adjacent, dispensed body for cut-separation from the chain, and for grasping by hand when handling a desired body that has been cut-separated from the chain; and wherein each body has a generally slender, finger-like configuration, and said handle-positioner structure has a generally broad-expanse, bar-like shape the long axis of which is transverse to the long axis of the body for promoting both the hand-holdable and positioning features of that structure.

2. The chain of claim 1, wherein each body includes a cut region located opposite the end including the handle-positioner structure, with the cut region being constructed to facilitate cut-separation of one body from another in that region.

3. The chain of claim 2, wherein each cut region takes the form of a zone of reduced dimensions in an area of the body corresponding to the cut region.

4. The chain of claim 3, wherein said tools take the form of intra-oral orthodontic units.

5. A chain of elongate, homogeneous, hand-holdable, tool-dispensing medical devices that can be dispensed from an associated dispenser for cut-separation of a desired device from the chain, comprising:

plural, interconnected, cut-separable, elongate carrier bodies, each including a central, elongate finger portion, and joined to one end thereof elongate, integral, handle-positioner-structure forming a generally T-shaped configuration with its associated finger portion, and a supply of medical tools formed integrally with and detachably joined to each of said finger portions.

* * * * *